United States Patent
Kumagai et al.

(10) Patent No.: US 9,677,940 B2
(45) Date of Patent: Jun. 13, 2017

(54) APPARATUS FOR ANALYZING ELEMENTS IN LIQUID WITH CONTROLLED AMOUNT OF GAS SUPPLY FOR PLASMA GENERATION

(71) Applicant: PANASONIC CORPORATION, Osaka (JP)

(72) Inventors: Hironori Kumagai, Osaka (JP); Shin-ichi Imai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 369 days.

(21) Appl. No.: 14/184,233

(22) Filed: Feb. 19, 2014

(65) Prior Publication Data
US 2014/0168644 A1 Jun. 19, 2014

Related U.S. Application Data

(63) Continuation of application No. PCT/JP2013/003077, filed on May 14, 2013.

(30) Foreign Application Priority Data

Jun. 28, 2012 (JP) ................ 2012-145843

(51) Int. Cl.
G01J 3/443 (2006.01)
G01N 21/67 (2006.01)
G01N 21/69 (2006.01)

(52) U.S. Cl.
CPC .............. G01J 3/443 (2013.01); G01N 21/67 (2013.01); G01N 21/69 (2013.01)

(58) Field of Classification Search
CPC .......... G01N 21/67; G01N 21/69; G01J 3/443
See application file for complete search history.

(56) References Cited

U.S. PATENT DOCUMENTS

| 5,464,513 | A | 11/1995 | Goriachev et al. |
| 5,630,915 | A | 5/1997 | Greene et al. |
| 7,875,825 | B2 | 1/2011 | Takamura et al. |
| 9,540,262 | B2 * | 1/2017 | Kumagai ............ C02F 1/4608 |
| 2007/0164003 | A1 | 7/2007 | Takamura et al. |

(Continued)

FOREIGN PATENT DOCUMENTS

| CN | 1818622 A | 8/2006 |
| CN | 100567964 C | 12/2009 |

(Continued)

OTHER PUBLICATIONS

International Search Report issued in International Application No. PCT/JP2013/003077 with Date of mailing Aug. 13, 2013, with English Translation.

(Continued)

*Primary Examiner* — Kara E Geisel
*Assistant Examiner* — Violeta A Prieto
(74) *Attorney, Agent, or Firm* — McDermott Will & Emery LLP

(57) ABSTRACT

An elemental analysis apparatus 101 includes a treatment vessel 108 of which at least a part is optically transparent, a first electrode 104 covered by insulator 103, a second electrode 102, a bubble-generating part which generates a bubble 106, a gas-supplying apparatus 105 which supplies gas to the bubble-generating part in an amount necessary for generating the bubble 106, a power supply 101 which applies voltage between the first electrode 104 and the second electrode 102, and an optical detection device 110 which determines an emission spectrum of plasma that is generated by application of the voltage, and the apparatus conducts qualitatively or quantitatively analysis of a component contained in the liquid 109 based on the emission spectrum determined by the optical detection device 110.

13 Claims, 13 Drawing Sheets

(56) References Cited

U.S. PATENT DOCUMENTS

| | | | | |
|---|---|---|---|---|
| 2013/0333841 A1* | 12/2013 | Narita | .................. | H05H 1/2406 156/345.26 |
| 2014/0014516 A1* | 1/2014 | Kumagai | .............. | C02F 1/4608 204/556 |
| 2014/0054242 A1* | 2/2014 | Imai | ...................... | C02F 1/4608 210/748.17 |
| 2014/0231329 A1* | 8/2014 | Imai | ...................... | C02F 1/4608 210/192 |
| 2015/0009496 A1* | 1/2015 | Kumagai | ............... | G01N 21/67 356/316 |
| 2015/0102255 A1* | 4/2015 | Imai | ...................... | C02F 1/4608 252/175 |
| 2015/0191371 A1* | 7/2015 | Fujikane | ................ | B01J 19/088 210/748.17 |

FOREIGN PATENT DOCUMENTS

| | | | | |
|---|---|---|---|---|
| CN | 102183508 A | 9/2011 | | |
| JP | H09-26394 A | 1/1997 | | |
| JP | H09-507428 A | 7/1997 | | |
| JP | 2002-372495 A | 12/2002 | | |
| JP | 3932368 B2 | 6/2007 | | |
| JP | 2007-207540 A | 8/2007 | | |
| JP | 2007207540 A | * | 8/2007 | |
| JP | 2011-180045 A | 9/2011 | | |
| JP | WO 2012157034 A1 | * | 11/2012 | ............ C02F 1/4608 |
| WO | 2005/093394 A1 | 10/2005 | | |

OTHER PUBLICATIONS

Translation of the International Preliminary Report on Patentability dated Jan. 8, 2015, issued in corresponding International Application No. PCT/JP2013/003077. 8 pgs.

Chinese Office Action and Search Report issued in Chinese Patent Application No. 201380002834.X dated Apr. 13, 2015, with English Translation.

Chinese Office Action dated May 30, 2016 issued in Chinese Patent Application No. 201380002834.X (English translation).

* cited by examiner (a)

Absence of bubble (b)

Presence of bubble (a)

(b)

(c)

APPARATUS FOR ANALYZING ELEMENTS IN LIQUID WITH CONTROLLED AMOUNT OF GAS SUPPLY FOR PLASMA GENERATION

CROSS REFERENCE TO RELATED APPLICATIONS

This is a continuation application of PCT Application No. PCT/JP2013/003077, filed on May 14, 2013, designating the United States of America, which claims the priority of Japanese Patent Application No. 2012-145843 filed on Jun. 28, 2012, the disclosure of which, including the specifications, drawings, and claims, are incorporated herein by reference in their entireties.

BACKGROUND OF THE INVENTION

The present invention is related to an apparatus for analyzing elements which exist in liquid by generating plasma in the liquid.

Conventional elemental analysis apparatuses which use plasma are described in WO 2005/093394 A, JP H09-26394 A and JP 2002-372495 A. Each of these documents discloses a method for analyzing elements wherein light emission coming from the elements in liquid, which is caused by action of plasma, is detected.

Plasma generation methods employed in the respective documents are different from each other. In WO 2005/093394 A, the plasma is generated by applying electric field to a micro-machined flow channel, specifically, a flow channel of an insulating material wherein a narrow portion of which cross section is significantly smaller than that of the flow channel is provided. In JP H09-26394 A, the plasma is generated by conducting so-called discharge on water. In JP 2002-372495 A, the plasma is generated by irradiation of laser.

SUMMARY OF THE INVENTION

An object of the present invention is to provide an apparatus for analyzing elements in liquid, which enables high-sensitive elemental analysis to be conducted with ease.

One embodiment of the present invention is an elemental analysis apparatus including:

a first electrode of which at least a part is placed in a treatment vessel that is to contain liquid, a second electrode of which at least a part is placed in the treatment vessel, a bubble-generating part which generates a bubble in the liquid when the liquid is contained in the treatment vessel, such that at least surface where conductor is exposed, of a surface of the first electrode which surface is positioned in the treatment vessel, is positioned within the bubble, a gas-supplying apparatus which supplies gas in an amount necessary for generating the bubble from the outside of the treatment vessel to the bubble-generating part, a power supply which applies voltage between the first electrode and the second electrode, and an optical detection device which determines an emission spectrum of plasma that is generated by application of the voltage, wherein at least a part of the treatment vessel is optically transparent, and a component contained in the liquid that is to be contained in the treatment vessel is qualitatively or quantitatively analyzed based on the emission spectrum determined by the optical detection device.

The elemental analysis apparatus of the above-mentioned embodiment makes it possible to analyze the elements contained in the liquid with higher sensitivity. Further, this embodiment can provide an apparatus for analyzing elements in liquid, which is excellent in portability.

BRIEF DESCRIPTION OF THE DRAWINGS

FIG. 1-2 is a spectrum in an example of the first embodiment.

FIG. 1-3 is a sectional side view wherein vicinity of an opening portion of an electrode in a variation of the first embodiment is enlarged.

FIG. 2 is a configuration view of an elemental analysis apparatus in a second embodiment.

FIG. 3 is a configuration view of an elemental analysis apparatus in a third embodiment.

FIG. 3-2 is a spectrum when He is used for forming a bubble

FIG. 4-2 shows a view illustrating that detection of plasma light varies depending on installation position of an optical detection device.

FIG. 4-3 is a view showing results of an example wherein the detection of plasma light varies depending on the installation position of the optical detection device.

Figure 1:
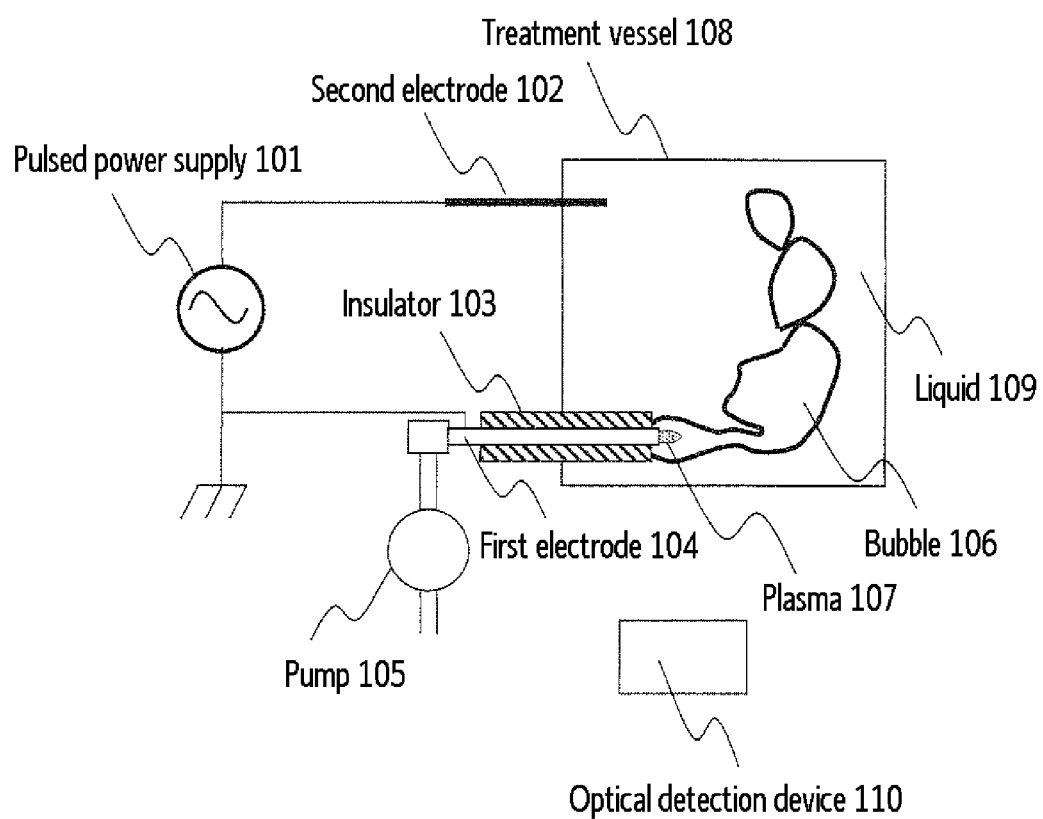
FIG. 1 is a configuration view of an elemental analysis apparatus in a first embodiment.

DETAILED DESCRIPTION OF EMBODIMENTS (Circumstances where a First Mode of the Present Invention was Obtained)

WO 2005/093394 A does not disclose a method for generating plasma without using a specially-machined cell and the technique described in WO 2005/093394 A has a problem of necessity for preparation of a special cell. WO 2005/093394 A describes that it is preferable to adjust the conductivity of a solution for plasma generation when the solution has a low conductivity. In that point, WO 2005/093394 A has a problem of cumbersome preparation for determination. Although the determination apparatus described in JP H09-26394 A can generate plasma with relative ease by conducting discharge on water, the plasma mainly generates light in air and interaction between the plasma and liquid is limited to a portion where the plasma contacts with liquid, resulting in relatively small plasma-light emission. For this reason, the determination apparatus described in JP H09-26394 A has a problem of difficulty in obtaining sensitivity necessary for elemental analysis. The analysis apparatus described in JP 2002-372495 A requires a laser for plasma generation to be prepared separately, and therefore has a problem of complicated apparatus construction.

The present inventor studied intensively and succeeded in generation of plasma in liquid with ease by generating a gas flow in the liquid. This does not require preliminary adjustment of, in particular, liquid for plasma discharge and makes it possible to generate large plasma with low power consumption of tens of watts or less. Further, the elemental analysis can be made from an emission spectrum of the plasma which is generated in the liquid according to this method.

(First Mode)

A first mode of the present invention is an elemental analysis apparatus including:

a first electrode of which at least a part is placed in a treatment vessel that is to contain liquid, a second electrode of which at least a part is placed in the treatment vessel, a bubble-generating part which generates a bubble in the liquid when the liquid is contained in the treatment vessel, such that at least surface where conductor is exposed, of a surface of the first electrode which surface is positioned in the treatment vessel, is positioned within the bubble, a gas-supplying apparatus which supplies gas in an amount necessary for generating the bubble from the outside of the treatment vessel to the bubble-generating part, a power supply which applies voltage between the first electrode and the second electrode, and an optical detection device which determines an emission spectrum of plasma that is generated by application of the voltage, wherein at least a part of the treatment vessel is optically transparent, and a component contained in the liquid that is to be contained in the treatment vessel is qualitatively or quantitatively analyzed based on the emission spectrum determined by the optical detection device. Since the invention according to this mode makes it possible to generate plasma easily with low power consumption, the element(s) in liquid can be analyzed easily. Further, since the plasma is generated with low power consumption, vaporization of the component contained in the electrode is eliminated or reduced, whereby the spectrum coming from the electrode can be eliminated or reduced in the emission spectrum of the plasma. In particular, this effect is remarkable when the electrode is formed of a metal having a high melting point, such as tungsten.

(Second Mode)

A second mode of the present invention is an elemental analysis apparatus including:

a first electrode and a second electrode, a gas-supplying apparatus which supplies gas, a bubble-generating part which generates a bubble, a power supply which applies voltage between the first electrode and the second electrode, and an optical detection device which determines an emission spectrum of plasma that is generated by application of the voltage, wherein at least a part of the first electrode and at least a part of the second electrode are adapted to be immersed in liquid simultaneously, the bubble-generating part supplies gas supplied by the gas-supplying apparatus into the liquid when the at least a part of the first electrode is immersed in the liquid and generates a bubble in the liquid such that at least surface where conductor is exposed, of a surface of the first electrode which surface is positioned in the liquid, is positioned within the bubble, and a component contained in the liquid is qualitatively or quantitatively analyzed based on the emission spectrum determined by the optical detection device.

In the case where the analysis apparatus as the first mode has a construction wherein the electrode is attached to the treatment vessel, a step of putting liquid which is an object of analysis into the treatment vessel is necessary. This may not meet a need of conducting determination anytime and anywhere. The elemental analysis apparatus according to this mode has a construction wherein at least a part of the first electrode and at least a part of the second electrode can be immersed in the liquid, and is excellent in portability. According to this embodiment, the elemental analysis can be made anytime and anywhere with ease by immersing the at least a part of the first electrode and the at least a part of the second electrode into the liquid which is an object of analysis.

(Third Mode)

A third mode of the present invention is the elemental analysis apparatus according to the first mode or the second mode, which further includes a gas-selection apparatus which enables different gases to be supplied by the gas-supplying apparatus.

When the gas is introduced to generate the bubble which covers the surface where the conductor of the first electrode is exposed in the liquid in the elemental analysis apparatus according to the first or the second mode, there is a problem of light emission coming from the introduced gas, in the plasma. For example, when air is introduced as the gas, no small light emission coming from nitrogen and oxygen is observed. For this reason, the detection sensitivity is reduced when the emission wavelength of the elements which is intended to be detected and the emission wavelength of the gas are overlapped. This mode makes it possible to select a type of gas which forms the bubble, whereby generation of light, due to the gas, having a wavelength that overlaps with the wavelength of the light emitted by the element which is an object of qualitative or quantitative analysis, is prevented. Thus, the present mode can increase the determination sensitivity.

(Fourth Mode)

A fourth mode of the present invention is the elemental analysis apparatus according to any of the first to the third modes, wherein the optical detection device is disposed in a direction which is different from a direction in which the bubble advances by buoyance as viewed from the first electrode, for example, a direction at 90° or greater with the direction in which the bubble advances by buoyance.

In the case where the bubble is formed and the plasma is generated within the bubble, the light emitted from the plasma is refracted or scattered at the interface between the bubble and the liquid. Further, since the bubble is separated and remains in the liquid for a while after the bubble covers the conductor portion of the first electrode, the plasma light is also refracted and scattered at the interface between the separated bubble and the liquid. The bubble in the liquid changes randomly through time, and this change causes the change in refraction and scatter of the plasma light at the gas-liquid interface. For this reason, the intensity of the plasma light which enters the previously-fixated optical detection device is varied, resulting in variation in detection sensitivity.

The fourth mode selects the position of the optical detection device such that the number of the bubbles through which the plasma light passes before it reaches the optical detection device is reduced. According to this embodiment, the random reflection and refraction of the plasma light due to the change in shape, number and distribution of the bubbles which exist between the plasma light and the optical detection device, is prevented or reduced, whereby the determination sensitivity can be improved.

(Fifth Mode)

A fifth mode of the present invention is the elemental analysis apparatus according to any one of the first to the fourth modes, wherein, the first electrode is of a hollow shape having an opening portion, insulator is positioned in contact with an outer peripheral surface of the first electrode, the bubble-generating part generates the bubble from the opening portion of the first electrode, and the bubble-generating part generates the bubble such that surface where the insulator is not positioned and the conductor is exposed, of the surface of the first electrode which surface is positioned in the treatment vessel, is positioned within the bubble. This construction makes it possible to generate the plasma with more ease.

(Sixth Mode)

A sixth mode of the present invention is the elemental analysis apparatus according to the fifth mode, wherein the insulator is optically transparent. This construction can prevent the plasma light to be absorbed by the insulator, and thereby the light can be detected efficiently.

(Seventh Mode)

A seventh mode of the present invention is the elemental analysis apparatus according to the sixth mode, wherein the insulator contains quartz. This construction can prevent the light in ultraviolet region to be absorbed by the insulator. Further, an apparatus having high resistance to the plasma can be provided.

(Eighth Mode)

An eighth mode of the present invention is the elemental analysis apparatus according to the first or the second mode, which further includes:

a bubble detection device which detects that the at least surface where conductor is exposed, of the first electrode is positioned within the bubble, or detects shape of the bubble, a control apparatus which controls any one or combination of the gas-supplying apparatus, the power supply and the optical detection device based on the detection result of the bubble detection device. In this construction, for example, when exposure of the optical detection device is controlled, the exposure of the optical detection device while the plasma light is not generated can be suppressed, and thereby the determination sensitivity of the analysis apparatus can be further improved.

(Ninth Mode)

A ninth mode of the present invention is the elemental analysis apparatus according to the eighth mode, wherein the optical detection device consists of two or more optical detection devices, and the control apparatus controls the two or more optical detection devices based on the detection result of the bubble detection device, such that one or more of the optical detection devices detect the emission spectrum. According to this construction, the analysis of higher sensitiveness can be made.

(Tenth Mode)

A tenth mode of the present invention is an elemental analysis method including:

immersing at least a part of a first electrode and at least a part of a second electrode in liquid, applying voltage between the first electrode and the second electrode which are immersed in the liquid, with use of a power supply, supplying a gas to a bubble-generating part disposed in the liquid by a gas-supplying apparatus to generate a bubble in the liquid, wherein the bubble is generated such that at least surface where conductor is exposed, of a surface of the first electrode which surface is positioned in the liquid, is positioned within the bubble, plasma is generated within the bubble by the application of the voltage, and an emission spectrum of the plasma generated within the bubble is determined by the optical detection device and a component contained in the liquid is qualitatively or quantitatively analyzed based on the emission spectrum.

(Eleventh Mode)

An eleventh mode of the present invention is the elemental analysis method according to the tenth mode, which further includes disposing the optical detection device in a direction different from a direction in which the bubble advances by buoyance as viewed from the first electrode. This analysis method is conducted using, for example, the elemental analysis apparatus of the second mode and includes selecting the position of the optical detection device such that the number of the bubbles which interfere until the plasma light reaches the optical detection device is reduced. This method enables the elemental analysis to be conducted with higher determination sensitivity.

(Twelfth Mode)

A twelfth mode of the present invention is the elemental analysis method according to the tenth or the eleventh mode which further includes:

selecting the gas to be supplied to the bubble-generating part from a plurality of gases, and supplying the selected gas to the bubble-generating part by the gas-supplying apparatus. This elemental analysis method is conducted using, for example, the elemental analysis apparatus according to the third mode. This elemental analysis method is conducted using the elemental analysis apparatus of the third mode.

Embodiments of the present invention will be described with reference to the drawings.

(First Embodiment)

In this embodiment, a basic mode for carrying out elemental analysis wherein plasma is generated in the liquid, is described.

FIG. 1 is a configuration view showing the configuration of an elemental analysis apparatus according to the present embodiment. A part of an electrode 102 and a part of an electrode 104 are disposed in to-be-treated water 109 filling an optically transparent treatment vessel 108. The treatment vessel 108 is not required to be optically-transparent entirely. A portion of the treatment vessel 108, which is positioned on a path along which the plasma light advances until it reaches the optical detection device 110, is necessary to be transparent to the extent that the plasma light passes the portion to allow the optical detection device 110 to detect an emission spectrum of the light. In the present embodiment, the electrode 104 has a hollow structure with the both ends opened, and an opening portion at one end, which is opposite to the other opening portion positioned in the water, is connected to a pump 105 as a gas-supplying apparatus. A bubble is generated from the opening portion positioned in the water. The electrode 104 also functions as a bubble-generating part in the present embodiment.

Materials for the first electrode 104 and the second electrode 102 are not limited particularly, and any metal or alloy may be used. These electrodes may be formed of, for example, iron, tungsten, copper, aluminum, or platinum, or an alloy containing one or more metals selected from these metals. In particular, when the first electrode 104 is formed of tungsten or platinum, or an alloy containing one or more metals selected from these metals, the spectrum coming from the electrode can be eliminated or reduced in the emission spectrum of the plasma light since tungsten and platinum have high melting points and are stable.

In the present embodiment, insulator 103 is positioned on an outer peripheral surface of the electrode 104. Alumina ceramics, insulating plastics, glass and quartz may be used as the insulator. As described below, when the plasma is generated with an end face of the electrode 104 being retracted inwardly from the end face of the insulator 103, the plasma is also generated at the inside from the end face of the insulator 103 and the plasma light is also emitted at the inside from the end face of the insulator 103. It is preferable that the insulator 103 is optically transparent relative to the light of wavelength range to be determined to allow the light to pass therethrough, so that the light emitted at the inside can be detected by the optical detection device 110. The optically transparent insulator is particularly quartz, but not limited to this.

The gas is supplied by the pump 105 via the electrode 104 into the liquid, whereby the bubble 106 is formed in the liquid. The bubble 106 is formed such that at least surface where the conductor is exposed, of the electrode 104 is positioned within the bubble. The end face of the opening portion of the first electrode 104 is not covered with the insulator 103 and exposes metal which is conductor. The state wherein the gas within the bubble 106 covers vicinity of the opening portion of the first electrode 104 can be maintained by optimally setting an amount of the supplied gas by the pump 105. The pump 105 functioning as the gas-supplying apparatus supplies the gas from the outside of the treatment vessel 108 to the first electrode 104 at a flow rate necessary for the at least surface where the conductor is exposed, of a surface of the first electrode 104 which surface is positioned within the treatment vessel, to be positioned within the bubble 106.

In the present embodiment, voltage is applied between the first electrode 104 and the second electrode 102 using a pulsed power supply 101. The power supply is not limited to the pulsed power supply, and a AC power supply or a DC power supply may be used as long as they enable the plasma to be formed within the liquid. Plasma 107 is formed within the bubble in the vicinity of the tip of the electrode 104 by the application of voltage. When the elements existing in the liquid contact with the plasma, light coming from the elements is generated. The elements in the liquid can be analyzed by detecting this light by the optical detection device 110 which is separately provided. For example, a combination of a PD (photodiode) and a spectrometer may be used as the optical detection device 110. The PD is used for detecting intensity of the light. For example, a CCD (Charge Coupled Device) and a CMOS (Complementary Metal Oxide Semiconductor) are used as the PD. A diffraction grating, a prism, and a filter may be used as the spectrometer. A PMT (Photomultiplier Tube) may be used instead of the PD and the optical detection device 110 may be composed of a combination of the PMT and the spectrometer The element which can be an object of the analysis is one which emits light of a peculiar wavelength in the plasma. Therefore, any of organic materials and inorganic materials may be the object of the analysis. For example, the components which can be the objects of the analysis are, for example, calcium, sodium and potassium. The analysis with use of the emission spectrum of the plasma light may be any of qualitative analysis and quantitative analysis. Therefore, the elemental analysis apparatus of the present invention can be used as a liquid analysis apparatus (for example, a water quality analysis apparatus).

The elemental analysis apparatus of the present embodiment may be used in a washing machine. In that case, hardness may be determined by determining a calcium concentration or a magnesium concentration in water and an amount of detergent may be adjusted depending on the hardness. Alternatively, the liquid analysis apparatus of the present embodiment may be used for managing a plant cultivation solution. Specifically, the apparatus may be used for analyzing a sodium amount or a potassium amount in the plant cultivation solution.

Figures 1, 2:
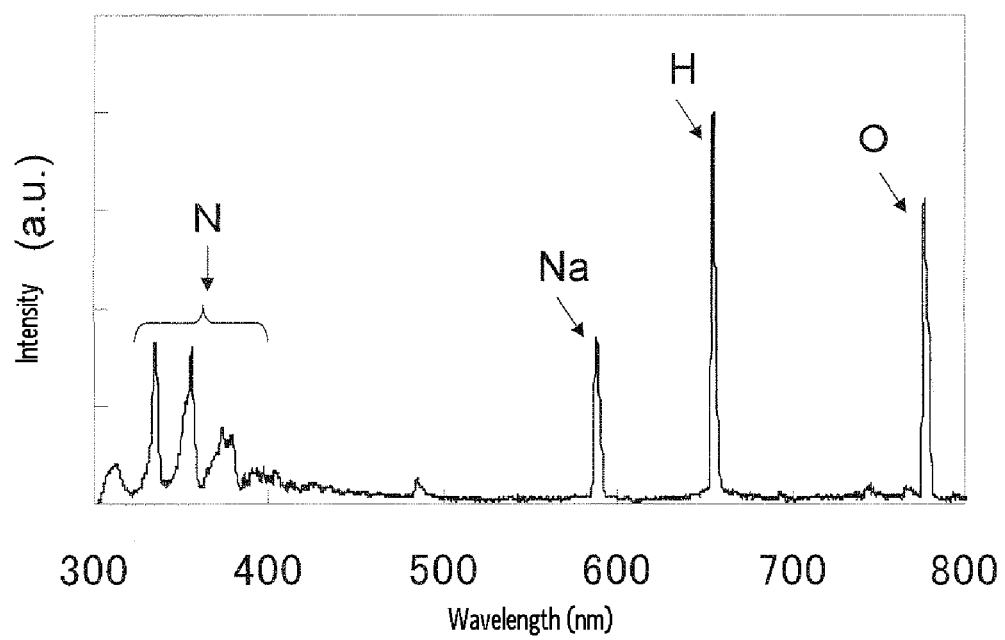
Figures 1, 2, 3:
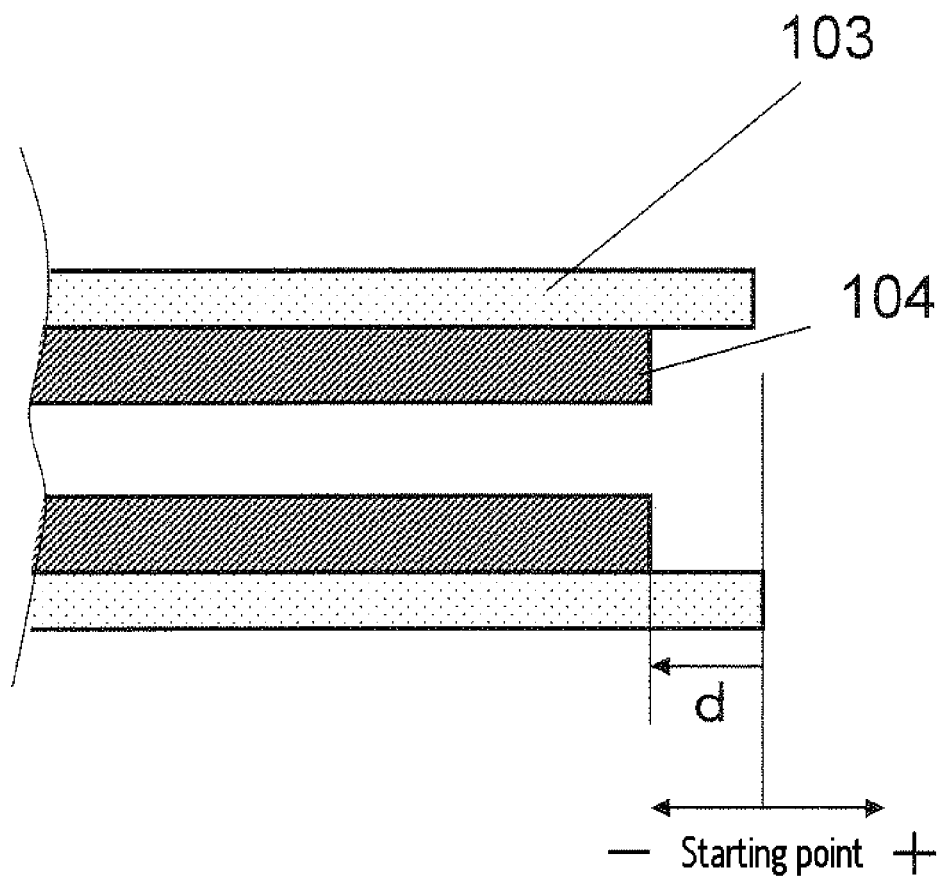
Figure 2:
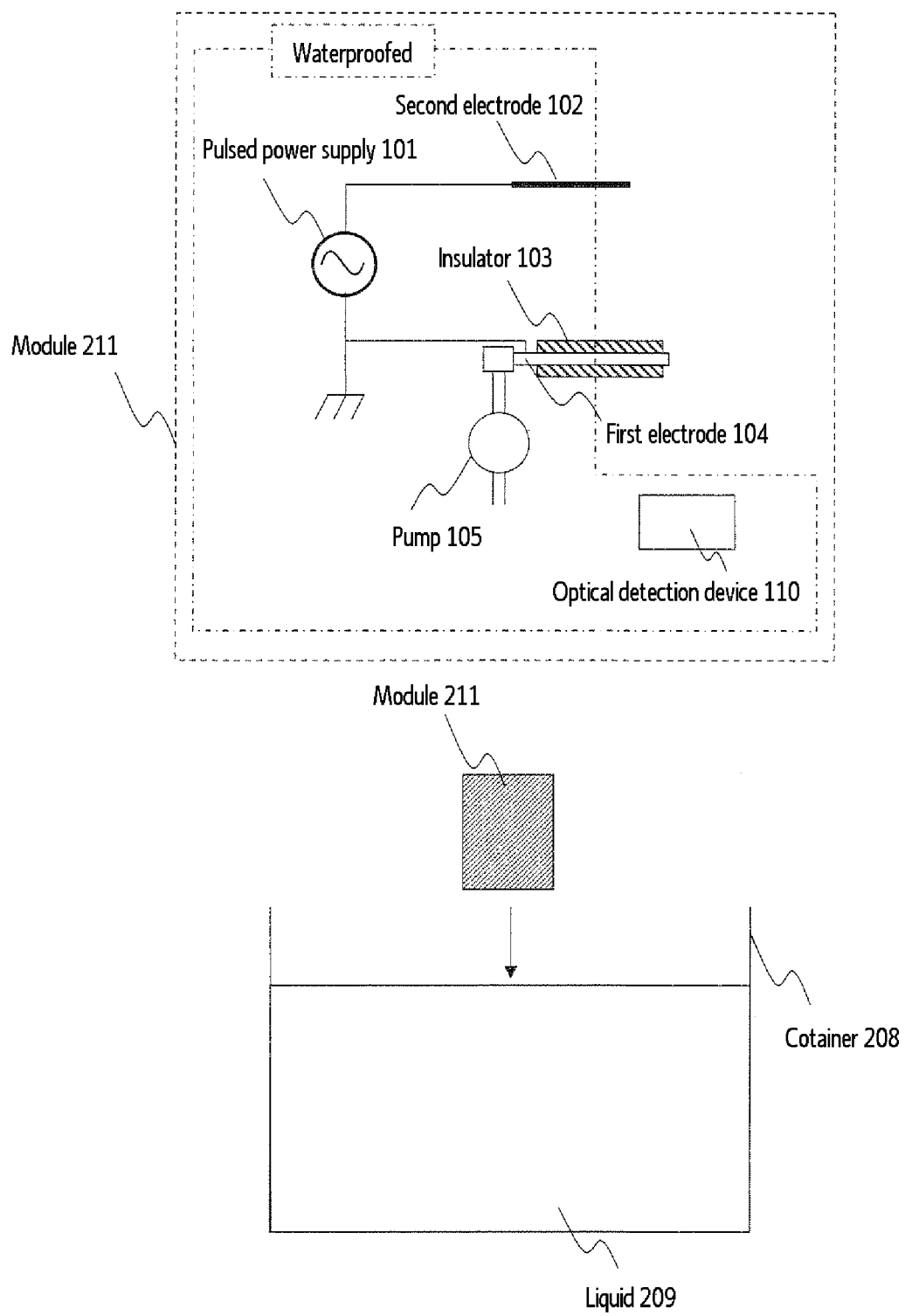
Figure 3:
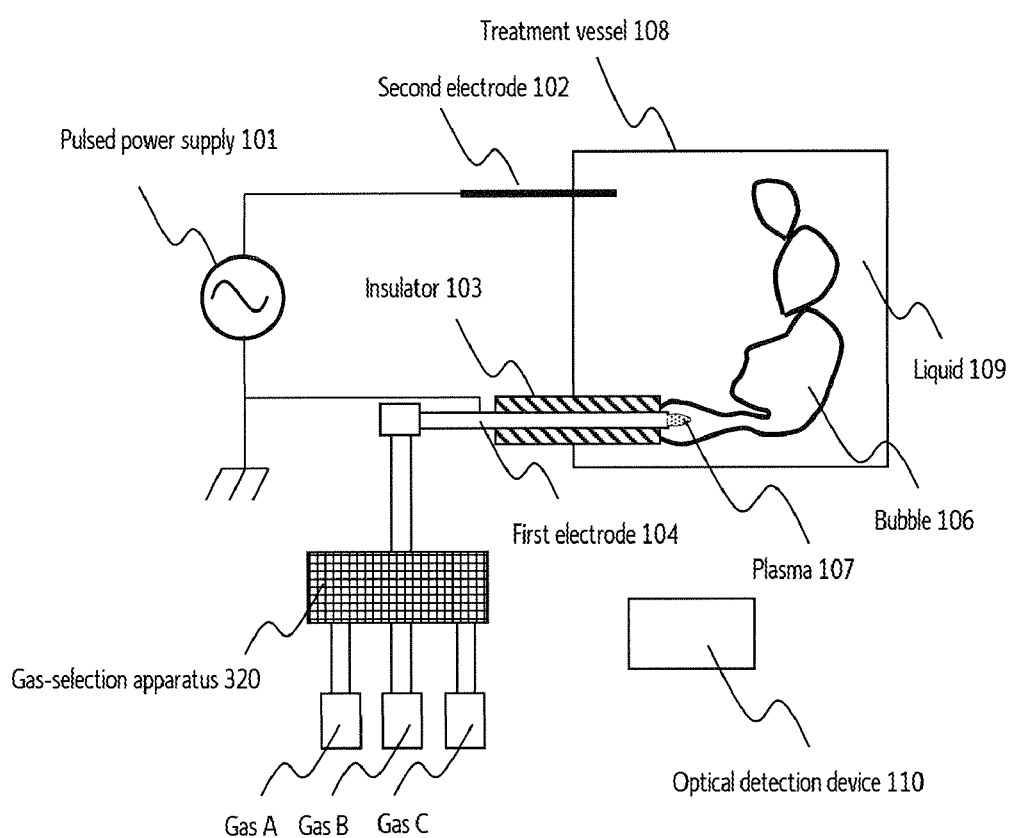
Figures 2, 3:
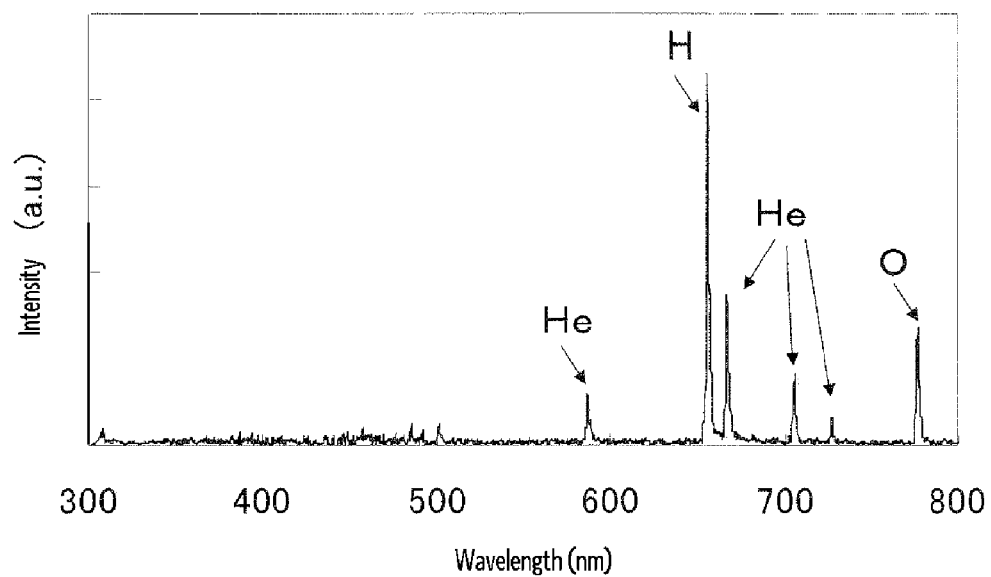

In a variation of the present embodiment, the insulator 103 may be positioned on the outer peripheral surface of the first electrode such that the end face of the insulator 103 is positioned outwardly from the end face of the first electrode 104 as shown in FIG. 1-3. For example, if the insulator 103 is configured slidably relative to the first electrode 104, a distance "d" between a tip of the insulator 103 and a tip of the first electrode 104 can be changed arbitrarily. When the insulator 103 and the first electrode 104 are disposed in this manner, a tip portion of the first electrode 104 is easily covered by the gas and the plasma can be generated efficiently.

EXAMPLES

The elemental analysis with the plasma light was conducted using the apparatus shown in FIG. 1. Here, the treatment vessel 108 having a capacity of 100 cm$^3$ was used. Further, the first electrode 104 was configured such that alumina having a thickness of 0.5 mm covered the outer peripheral surface of a tube of tungsten having an inner diameter of 1 mm and an outer diameter of 2 mm. The second electrode 102 was a columnar of tungsten having a diameter of 1 mm and was disposed about 40 mm away from the first electrode 104.

A solution of NaCl in pure water as the liquid 109 was put into the treatment vessel 108. A conductivity of the liquid was 300 mS/min. The bubble 106 was generated by introducing air from the outside using the pump 105 at a flow rate of 2.0 liter/min. Discharge was conducted by supplying power of 200 W and applying a pulsed voltage having a peak voltage of 4 kV, a pulse duration of 1 μs and a frequency of 30 kHz to the first electrode 104. The plasma was generated by this discharge and the emission spectrum of the plasma was determined by the optical detection device 110. A commercial spectroscopic system was used to determine the light of wavelength of 300 nm to 800 nm. The exposure time was 20 ms. An optical fiber which was provided with the spectroscopic system was installed outside the treatment vessel 108 of glass and around the place where the plasma is formed, and determined the emission spectrum of the plasma. The determined spectrum is shown in FIG. 1-2. A peak peculiar to Na appears in the vicinity of 589 nm and Na was detected. From this example, it was found that Na, which is impurity in pure water, could be detected by the present embodiment.

(Second Embodiment)

In the present embodiment, an elemental analysis apparatus as a module having no treatment vessel is described.

Although the configuration wherein the electrodes which generate the plasma and so on are disposed in the treatment vessel 108 in the first embodiment, the electrodes and so on are not necessarily required to be disposed in the treatment vessel. Thus, in the present embodiment, a mode is described, wherein the entire of a module 211 provided with elements for generating plasma and elements for detecting the plasma light is put in the liquid and an element is detected.

FIG. 2 is a configuration view of an elemental analysis apparatus according to the present embodiment. A module 211 corresponds to a construction which is obtained by removing the treatment vessel 108 and the to-be-treated water 109 from the first embodiment described with reference to FIG. 1. The second electrode 102 and the first electrode 104 are disposed such that, when the module 211 is put into the liquid, parts of the respective electrodes are immersed simultaneously in the liquid to contact with the liquid. All the elements constituting the present embodiment, except for the parts of the first electrode 104 and the second electrode 102 which are to be immersed in the liquid are subjected to waterproof process, or disposed in a housing which is subjected to waterproof process. Specifically, the elements which are contained in a region enclosed by a one-dotted chain line in FIG. 2 are subjected to the waterproof process or disposed in the housing which is subjected to waterproof process. Therefore, even if the entire module is immersed in the liquid, each element can be operated. The waterproof process can be conducted using a well-known method.

This module 211 is immersed in the liquid 209 contained in a container 208 and then plasma is generated. In the present embodiment, a construction is employed wherein the liquid 209 is contained in the container 208, but the container 208 is not essential. For example, when one wishes to determine the water quality of a river, the water quality can be determined by putting the module 211 into the river. The method for generating plasma is the same as that in the first embodiment. The present embodiment makes it possible to provide the elemental analysis apparatus which is excellent in portability.

Further, the present embodiment makes it possible to conduct two or more elemental analyses by moving the module to vary the depth or the place where the plasma is generated. This makes it possible to easily carry out mapping of impurity contained in the liquid.

A variation of the present embodiment has a construction wherein as long as a part of the first electrode and a part of the second electrode are immersed in the liquid to generate the plasma, one or more elements except for the first electrode and the second electrode are disposed outside the module and are not put into the liquid. For example, the pulsed power supply 101 may be disposed outside the module 211 and connected to the first electrode 104 and the second electrode 102 by a waterproof cable.

Alternatively, the optical detection device 110 may be disposed outside the module (for example, the outside of the container 208 shown in FIG. 2). Alternatively, a variation of the present embodiment may be of a construction wherein all the elements except for the first electrode and the second electrode are not put into the liquid.

Alternatively, in a variation of the present embodiment, another element not shown in the figure may be included in the module 211. For example, a gas cylinder as a gas-supplying source, which is connected to the pump 105 as the gas-supplying apparatus, may be disposed in the module 211.

Alternatively, when the bubble-generating part is provided separately from the first electrode in a variation of the present embodiment, the bubble-generating part is configured such that it is immersed in the liquid together with the first electrode and the second electrode.

(Third Embodiment)

In the present embodiment, a mode wherein the elemental analysis with high sensitivity is conducted using a gas-selection apparatus, is described.

FIG. 3 is a configuration view of an elemental analysis apparatus according to the present embodiment. The elemental analysis apparatus shown in FIG. 3 is different from the apparatus shown in FIG. 1 in that the pump 105 is connected to a gas-selection apparatus 320 and the gas-selection apparatus 320 is connected to gas-supplying sources A to C. In the apparatus shown in FIG. 3, any of the gases A to C selected by the gas-selection apparatus 320 is fed into the liquid via the first electrode 104 to form the bubble 106. The other construction is the same as that of the first embodiment.

For example, when the bubble 106 is formed using air, a light emission coming from the air, specifically the light emissions coming from oxygen and nitrogen are generated in no small measure. For example, in FIG. 1-2, the emission coming from nitrogen can be observed in the vicinity of 300 nm to 400 nm. Further, the emission coming from oxygen is generated around 777 nm. For this reason, high-sensitive determination is difficult to be made for the emission which comes from the elements in the liquid and overlaps with the light emission coming from the air. For example, it is difficult to observe the light emissions of Ca (317.9 nm), Cr (357.9 nm), and Cu (327.4 nm) and so on.

In the present embodiment, when the light emission coming from the gas and the light emission coming from the elements in the liquid are predicted to overlap with each other, a gas is selected using the gas-selection apparatus in order to avoid such overlap. A spectrum is shown in FIG. 3-2 wherein helium is employed as the gas. As shown in FIG. 3-2, the spectrum coming from helium is different from the spectrum shown in FIG. 1-2 in that light emission between 300 nm and 400 nm is smaller. Therefore, the use of helium is suitable for detecting the light emission coming from Ca, Cr or Cu. On the contrary, the spectrum around 588 nm is observed as the peak coming from helium. Therefore, the use of helium is not suitable for detecting Na having a spectrum around 589 nm as shown in the example of the first embodiment.

Therefore, in the present embodiment, when one previously knows that Ca should be detected, He is selected using the gas-selection apparatus 320. When one knows that Na should be detected, air is selected using the gas-selection apparatus 320. Then, the plasma is generated and the spectrum is detected. The same method for generating plasma as that in the first embodiment can be employed. Thereby, Ca and Na can be detected with high sensitivity.

In addition to helium and air, argon, nitrogen, oxygen and carbon dioxide can be used as the gas. The number of gases which can be selected by the gas-selection apparatus is not limited to three, and may be two or four.

Further, when two or more elements are intended to be detected and detection of any one of elements is interfered by the spectrum coming from the gas, the spectrums are obtained using a plurality of gases separately and the detection results are finally put together to obtain the analysis result for all the elements. For example, when Ca and Na are supposed to be mixed in the liquid, the spectrum coming from Ca can be firstly obtained selecting He and then the spectrum coming from Na can be obtained selecting air. The spectrums of both of Ca and Na can be determined with high sensitivity by putting the respective detection results together.

(Fourth Embodiment)

In the present embodiment, a mode wherein the elemental analysis is conducted with high sensitivity by selecting the installation position of the optical detection device, is described with reference to FIG. 4, FIG. 4-2 and FIG. 4-3.

Figure 4:
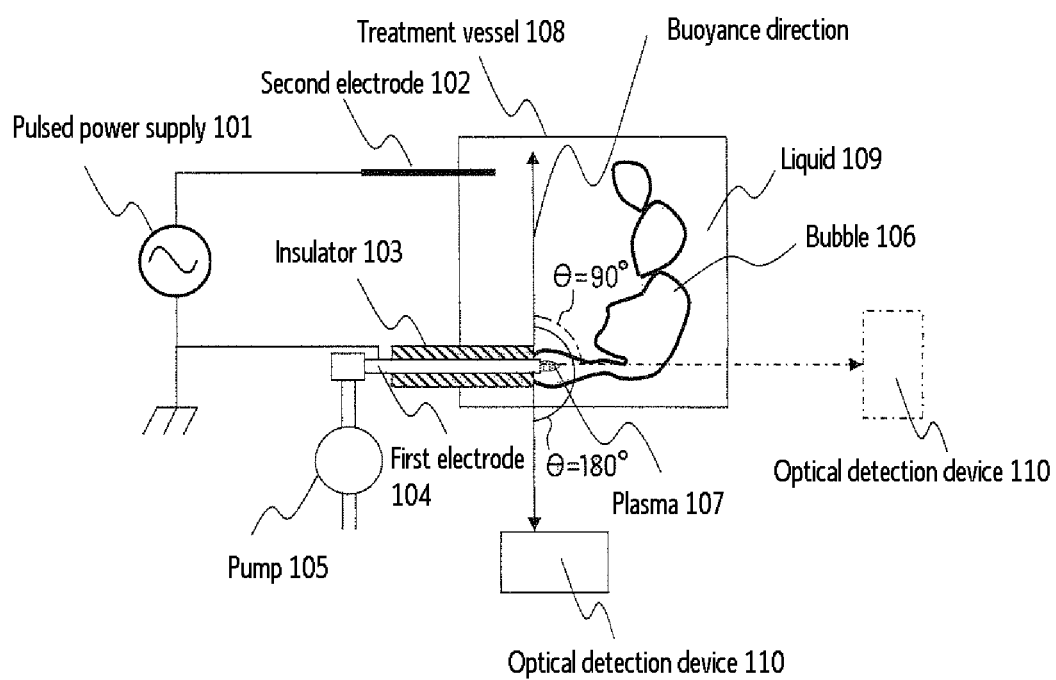
FIG. 4 is a configuration view of an elemental analysis apparatus in a fourth embodiment.
Figures 2, 4:
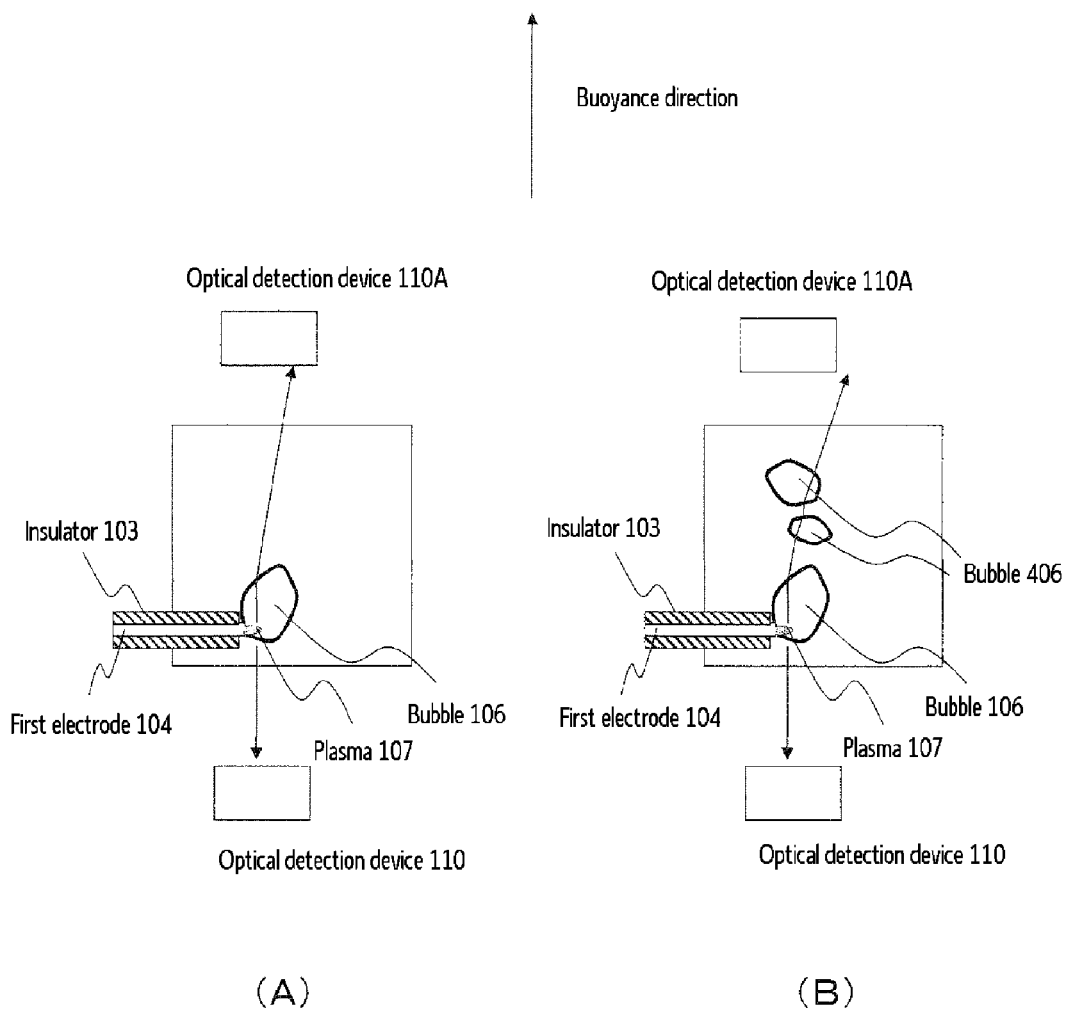
Figures 3, 4:
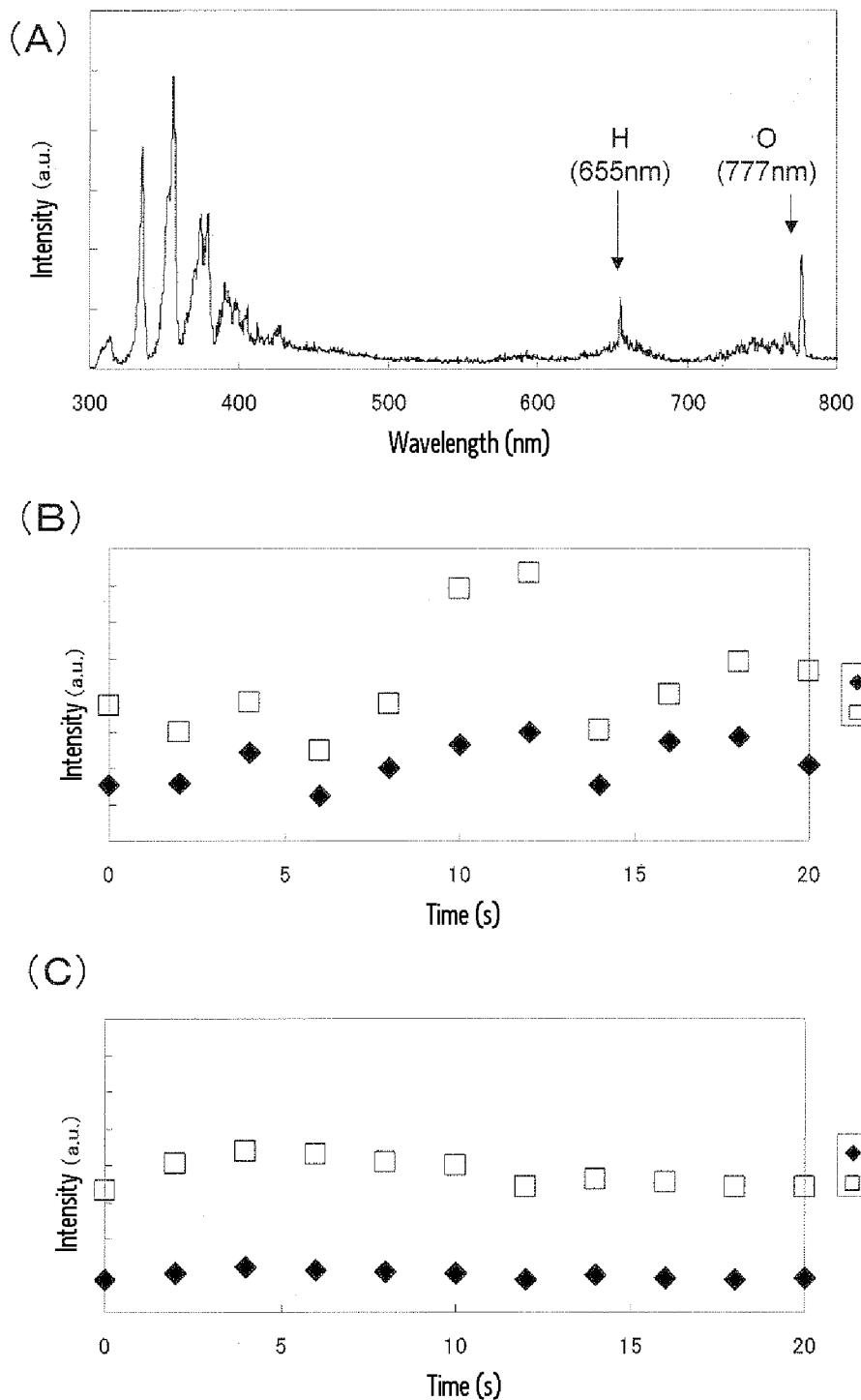

FIG. 4 is a configuration view of an elemental analysis apparatus according to the present embodiment. After the gas is introduced into the liquid, a bubble covering a surface where the conductor of the first electrode 104 is exposed, a bubble formed by separation of the bubble from the first electrode, and a bubble separated from the aforementioned bubbles move upwardly by buyoance. FIG. 4-2 shows views explaining that the stability of the plasma-light detection differs depending on the position where the optical detection device is installed. FIG. 4-2(A) shows the case where the bubble 106 exists only in the vicinity of the electrode. FIG. 4-2(B) shows the case where the bubble 106 and bubbles 406 after separation of the bubble 106 from the first electrode 104 move upwardly by buyoance. The light emission by the plasma formed within the bubble 106 refracts and scatters at the interface between the liquid and the gas until it reaches the optical detection device.

As shown in FIG. 4-2(A), when a single bubble exists, the number of refractions and scatters is small and therefore the light reaching the optical detection device 110A which is installed in a direction of the buyoance as viewed from the first electrode 104, is relatively stable. However, when many bubbles are formed and move upwardly by the buyoance, there are many bubbles in the direction of buyoance as viewed from the first electrode 104. Thereby the number of the interfaces between the liquid and the gas is increased and the number of refractions and scatters is increased by that. As a result, the optical detection device 110A placed in a direction in which the gas advances by the buyoance as viewed from the first electrode 104, may not detect the generated plasma light or the light which has been damped may reach the device. The shape and the number of bubbles formed by introduction of gas are relatively difficult to be controlled, and thus the interface between the liquid and the gas is also difficult. For these reasons, it is supposed that the elements in the liquid cannot be analyzed by the plasma light with high sensitivity when the optical detection device is installed in a direction in which the bubble advances by the buyoance.

On the other hand, in FIGS. 4-2(A) and 4-2(B), the number of bubbles is small and thus the number of refractions and scatters is small in a direction opposite to the direction in which the bubble advances by the buyoance as viewed from the first electrode 104 (below the first electrode 104). For this reason, when the optical detection device 110 is placed in this direction, the plasma light can be stably detected.

Therefore, in the present embodiment, the optical detection device is positioned in a direction which is different from the direction in which the bubble advances by the buyoance as viewed from the first electrode 104, for example, in a direction which makes 90° or grater, particularly 180° with the direction in which the bubble advances by the buyoance. Specifically, in FIG. 4, the optical detection device 110 may be placed at a position where $\theta=90°$ to a position where $\theta=180°$ More specifically, the optical detection device 110 may be placed such that a portion which detects the plasma light is disposed at a position which is indicated by a one-dotted chain line in FIG. 4. This is because the number of bubbles is small in a direction at which $\theta$ is 90° or greater. Alternatively, the optical detection device may be placed above or below a paper wherein the figure is drawn such that $\theta$ is, for example, 90° or greater.

The number of the interfaces between the liquid and the gas until the plasma light reaches the optical detection device 110 can be reduced and can be, for example, substantially one by arranging the optical detection device 110 in this manner. Thereby, since the refraction and the scatter can be predicted, the plasma light can be detected with high sensitivity by controlling the installation position of the optical detection device 110. In other words, the element in the liquid can be analyzed with high sensitivity.

In the configuration like the present embodiment wherein the treatment vessel 108 is provided, the optical detection device 110 can be previously installed in a direction different from the direction in which the bubble advances by the buyoance as viewed from the first electrode 104. In another embodiment, like the second embodiment, wherein the treatment vessel is not provided and an apparatus which includes a module to be immersed in the liquid is employed, it is difficult to decide the position of the optical detection device. In that case, the optical detection device may be placed at the position where the plasma light is stably detected after generating the bubble and confirming the direction of buyoance in the state where the electrodes immersed in the liquid. For example, the direction in which the light is stably detected may be found out based on refraction and scatter of a light from a lamp that is attached to the tip of the electrode, under the bubble generation.

Example

Result of an example is shown in FIG. 4-3 indicating that the detection of plasma light differs depending on the installation position of the optical detection device. The plasma light spectrum in pure water is shown in FIG. 4-3(A). Focusing attention on the intensity of light emissions of H (655 nm) and O (777 nm) shown in FIG. 4-3, variation in received light intensity of the optical detection device was determined during the discharge which was continued for 20 seconds. The determination was made for the case where the optical detection device was installed at the position where $\theta=0°$ in FIG. 4 and the case where the optical detection device is installed at the position where $\theta=90°$. FIG. 4-3(B) shows the received light intensity in the case of $\theta=0°$ and FIG. 4-3(C) shows the received light intensity in the case of $\theta=90°$.

As shown in FIG. 4-3(B), when $\theta=0°$, that is, the optical detection device is installed in almost the same direction as the buyoance direction of the bubble, it was confirmed that the received light intensity was significantly varied by the effect of the bubble which exist randomly. On the other hand, when $\theta=90°$, that is, the light was detected in a state where the number of interfaces between the liquid and the gas is small, it was confirmed that the received light intensity was stable during 20 seconds. As a result, the plasma light can be detected with high sensitivity to enable the elemental analysis by selecting the position of the optical detection device such that the received light intensity is stabilized.

(Fifth Embodiment)

In the present embodiment, a mode is described wherein a control apparatus 520 and a bubble-detection device 530 are added to the construction of the first embodiment and the control apparatus 520 controls the bubble-detection device 530 and the optical detection device 110. This embodiment is described using FIG. 5.

Since the presence or absence of the bubble and the shape of the bubble are changed randomly as time goes on, it is difficult to strictly control the interface between the bubble and the liquid.

In the elemental analysis apparatus of the present embodiment, the voltage is applied between the first electrode 104 and the second electrode to generate plasma within a bubble 106, when a surface of the first electrode 104 where the conductor is exposed to the liquid is covered by the bubble 106. For this reason, when the bubble 106 is not formed, the plasma is not generated, which means that the light from the plasma is not obtained. Then, the exposure time of the optical detection device 110 is required to be long in order to obtain the emission spectrum without missing the timing of plasma generation. However, when the exposure time is long, the detection amount of the optical detection device 110 may be saturated and therefore it is often necessary to narrow the exposure time of the optical detection device 110 to some extent. Specifically, processing wherein the signals of approximately a millisecond are accumulated and an average value of a plurality of signals is calculated, is made.

In the case where a conventional CCD is employed as the optical detection device 110, it does not mean that the light is detected being synchronized with the timing of discharge that is accidental on microscopic time scale. For this reason, when the bubble is not formed in the vicinity of the electrode 104 within a millisecond for which the exposure is made, an optical detection amount is almost zero, resulting in reduction in detection sensitivity. Therefore, the exposure of the optical detection device 110 is controlled by the control apparatus 520 in the case where the optical detection device 530 detects the bubble. Since this construction makes it possible to suppress the exposure while the light is not generated, the entire determination sensitivity (or the analysis sensitivity) of the apparatus can be improved.

Further, as described in the fourth embodiment, the state of refraction and scatter by the plasma light differs depending on the state of the interface between the bubble and the to-be-treated water. For this reason, the state of the plasma light detected by the optical detection device differs depending on the shape of the bubble.

Figure 5:
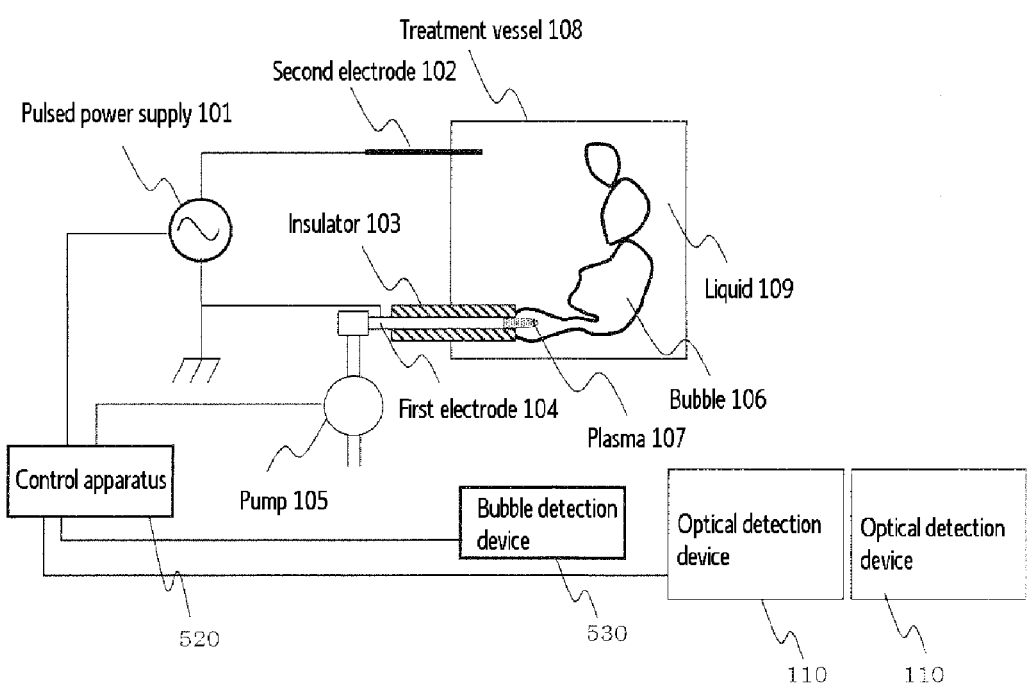
FIG. 5 is a configuration view of an elemental analysis apparatus in a fifth embodiment.

Thus, in the present embodiment, the presence and absence of the bubble, and the bubble shape are detected by the bubble detection device 530 and the control apparatus 520 controls the optical detection device 110 based on the detected results. For example, as shown in FIG. 5, a plurality of optical detection devices are installed (two devices are installed in FIG. 5) and the optical detection device 110 on the optical path that is predicted based on the bubble shape, is selected by the control apparatus 520. That is, the control apparatus 520 conducts control such that any one of the optical devices 110 detects the emission spectrum based on the detection results of the bubble detection device 530. This eliminates use of signals in the case of failure of plasma-light detection by the optical detection device, and therefore the elemental analysis can be conducted with high sensitivity.

The optical detection device 110 may be movable, although such device is not shown. In that case, the optical detection device 110 is moved to the optical path which is predicted based on the results from the optical detection device 530. High-sensitive elemental analysis can be conducted by doing so.

In the present embodiment, a high-speed camera can be used as the bubble detection device 530. The high-speed camera is set to focus on the bubble 106 in the vicinity of the first electrode 104. The bubble shape is judged using a predetermined algorithm and the judgment results are transferred to the control apparatus 520. The control apparatus 520 gives the feedback to the power supply 101 and the optical detection device 110 based on the judgment results of the bubble detection device 530. For example, whether or not the bubble 106 exists near the first electrode 104 is judged using a processing unit from the contrast of image which is taken by the high-speed camera, and the judgment results can be fed back to the control apparatus 520. Further, the optical path is predicted by detecting the bubble shape and the optical detection device 110 is selected which exists on the optical path. It is possible to use a known image-detecting method as the method for detecting the bubble. Thereby, it is possible to apply the voltage only when the bubble is present, resulting in elimination of wasteful power consumption, and also possible to conduct the elemental analysis with higher sensitivity.

Figure 6:
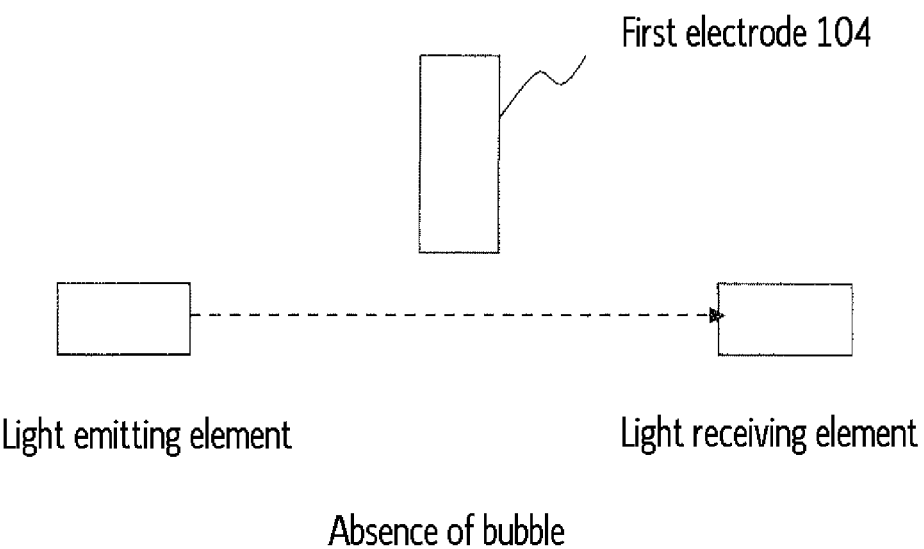
FIG. 6 is a view illustrating a method for detecting a bubble by a bubble detection device with a light-emitting element and a light-receiving element.
Figure 6:
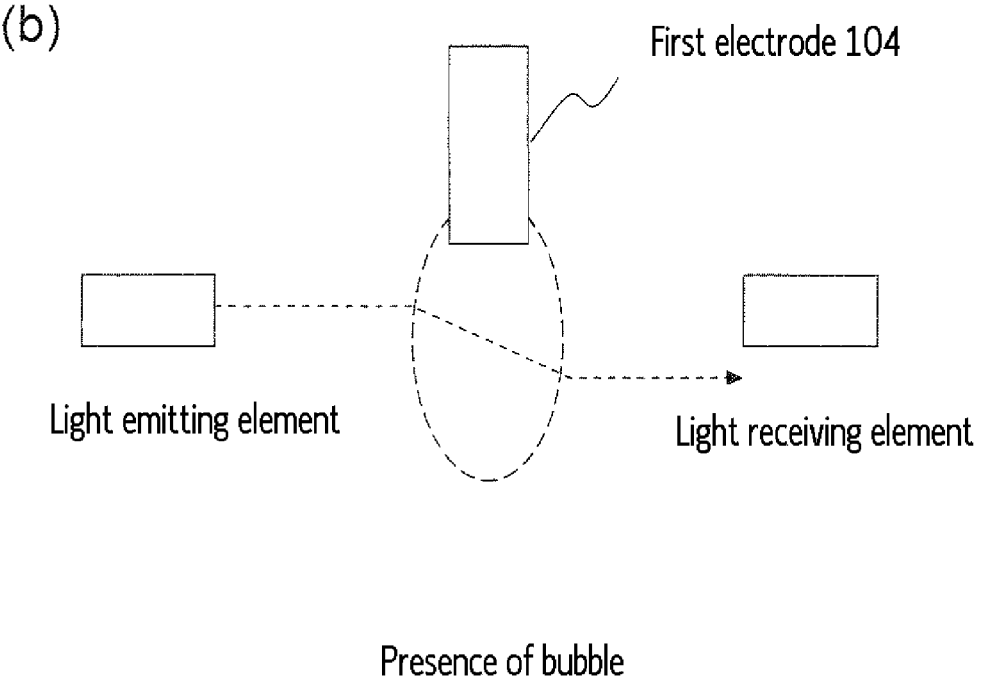

Alternatively, a light-emitting element and a light-receiving element can be used as the bubble detection device. For example, a semiconductor laser or a light-emitting diode (LED) may be used as the light-emitting element and a photodiode may be used as a light-receiving element. FIG. 6 schematically shows a method for detecting bubble by means of a bubble detection device wherein the light-emitting element and the light-receiving element are used. The light-emitting element is arranged such that an optical path of the laser is positioned near the bubble at the tip of the first electrode 104. The light-receiving element is positioned at a place where it can receive light when the bubble is absent (FIG. 6($a$)). When the bubble is generated, the refractive index is changed causing the laser optical path to be changed, and thereby the amount of light received by the light-receiving element is varied (FIG. 6($b$)). Although the plasma discharge generates light which may be a cause of interference with the light detection device, such interference can be avoided by selecting conditions in advance. For example, it is possible to set a wavelength of the semiconductor laser such that it does not interfere with the plasma discharge spectrum. A predetermined value is set as a threshold value and the signals of the light-receiving element are transmitted to the control apparatus. The control apparatus gives the feedback to the power supply based on the results of the bubble detection device. This makes it possible to eliminate wasteful power consumption. The use of the optical detection device makes it possible to construct the bubble detection device at a relatively low cost.

Figure 7:
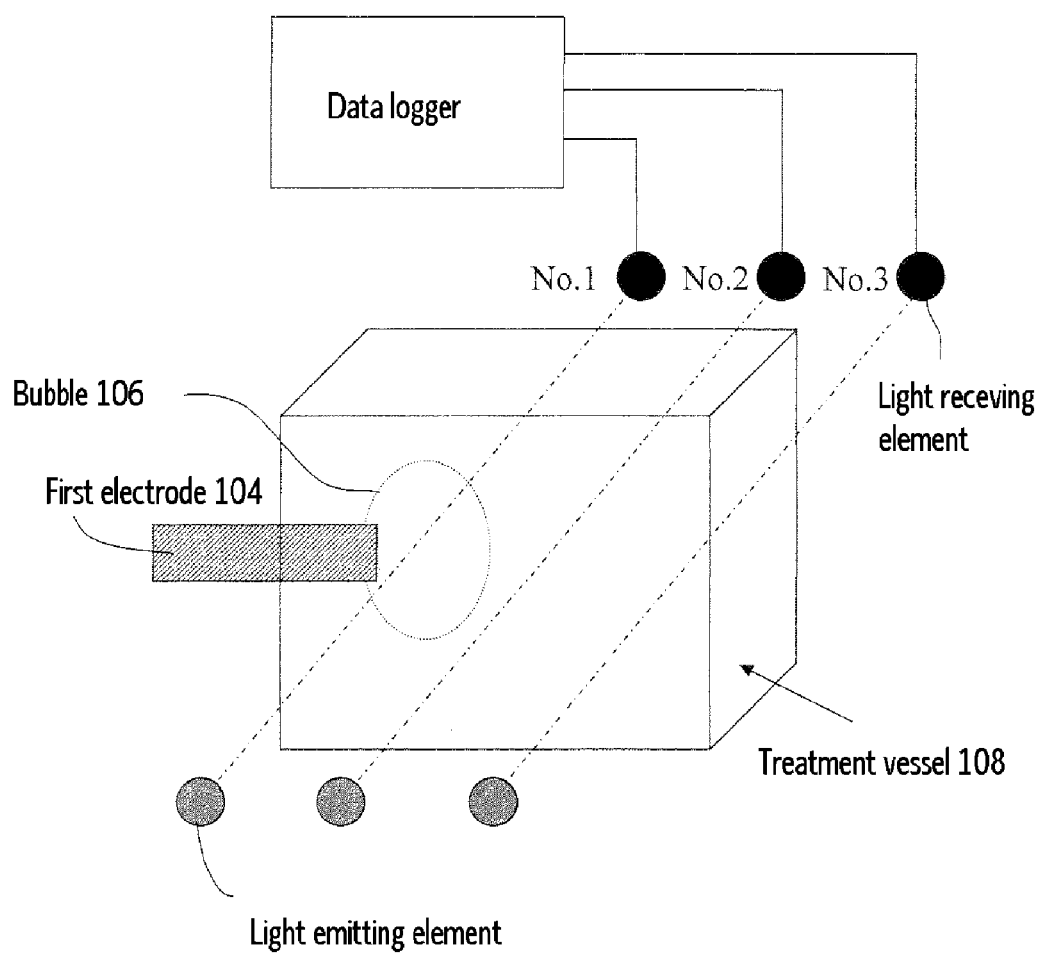
FIG. 7 is a schematic view showing another example of a bubble detection method wherein a light-emitting element and a light-receiving element are employed as a bubble detection device.

An example of bubble detection with use of a light-emitting element and a light-receiving element as the bubble detection device, will be described below. As shown in FIG. 7, a light-emitting diode was positioned on one side of a transparent treatment vessel such that the central optical path of the light emitting diode which was a light-emitting element (central wavelength 610 nm) was positioned near the bubble at the tip portion of the electrode. In addition, an illuminance sensor, as the light-receiving element, which received the light from the light-emitting diode and determined the light quantity thereof was positioned on the side opposite to the side on which the light-emitting diode was positioned such that the sensitivity of the sensor was maximized under the condition where the bubble was not present. Three pairs of light-emitting diode and illuminance sensor were placed as shown in FIG. 7. Further, a distance between adjacent pairs was 1 cm. In FIG. 7, the pairs of the light-emitting diode and the illuminance sensor are numbered as Nos. 1 to 3 from the position close to the electrode.

The voltage generated by the illuminance sensor is changed depending on the amount of received light. Then, the voltage generated by the illuminance sensor was detected using a commercial data logger, and the voltage change due to the presence or absence of bubble was determined. The determination was conducted with a 100 ms interval. No optical filter was used in the illuminance sensor. Introduction of bubble and a power supply for the light-emitting diodes are controlled as shown in Table 1.

TABLE 1

| Time (s) | Bubble generation | LED |
|---|---|---|
| 0-4 | Absent | OFF |
| 4-9 | Present | ON |
| 9-12.5 | Absent | ON |
| 12.5-20 | Present | ON |

Figure 8:
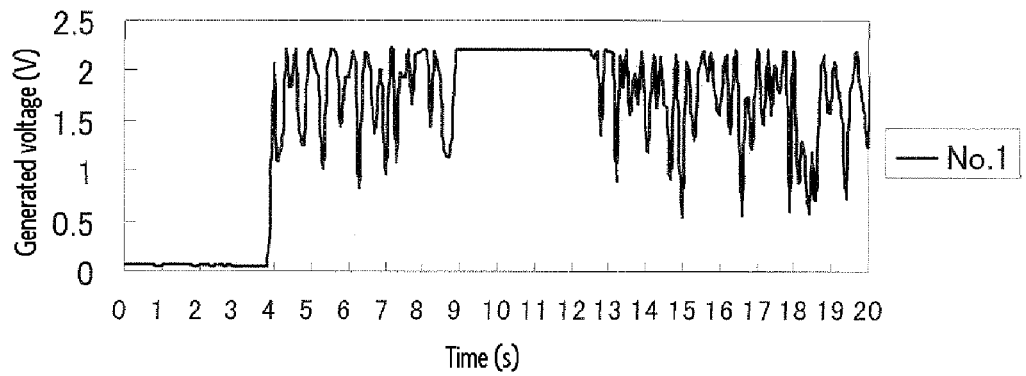
FIG. 8(a) is a graph showing change in light-emitting voltage of the light-receiving element of a pair referred to as "No. 1" in FIG. 7.
FIG. 8(b) is a graph showing change in light-emitting voltage of the light-receiving element of a pair referred to as "No. 2" in FIG. 7.
FIG. 8(c) is a graph showing change in light-emitting voltage of the light-receiving element of a pair referred to as "No. 3" in FIG. 7.
Figure 8:
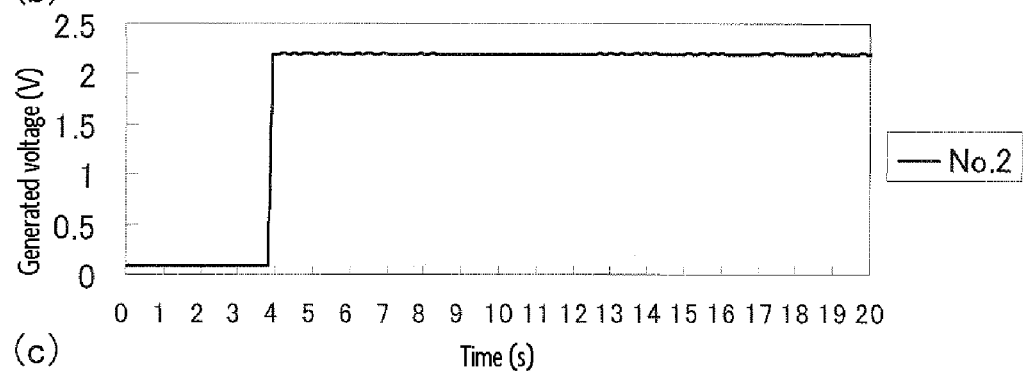
Figure 8:
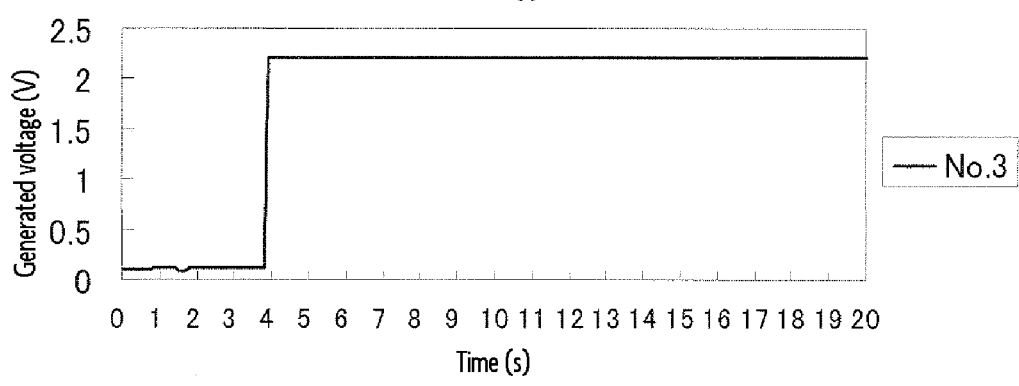

As shown in FIG. 8, the voltages generated by the illuminance sensors in Nos. 1 to 3 were almost 0 V in the region of 0 seconds to 4 seconds wherein the power supply was in the OFF state. Next, the gas was supplied from the outside and the power supply of the light emitting diode was switched ON in the region of 4 seconds to 9 seconds, it was confirmed that only the voltage generated by the illuminance sensor in No. 1 wherein the bubble was positioned in the optical path was varied according to the generation of bubble. Specifically, it was confirmed that the generated voltage varied between 0.5 V and 2.2V in accordance with the presence or absence of the bubble. The generated voltages by the illuminance sensors in Nos. 2 and 3 wherein the bubble was not positioned in the optical path, were constantly 2.2 V regardless of the presence or absence of the bubble.

Next, in the region of 9 seconds to 12.5 seconds, the gas supply was stopped while the power supply of the light-emitting diode was in the ON state. In that region, the generated voltage of the illuminance sensor in No. 1 was almost constantly 2.2 V similarly to those of the illuminance sensors in Nos. 2 and 3. Finally, the gas was again supplied in the region of 12.5 seconds to 20 seconds. In that region, only the generated voltage of the illuminance sensor in No. 1 was varied again in accordance with the generation of bubble. Therefore, it was possible to confirm that the light-emitting element and the light-receiving element was able to be used as the gas detection device by this example. In this example, the determination was conducted with a 100 ms interval because of the performance of the data logger. The detection sensitivity can be further improved by shortening the determination interval of the data logger.

In the above example, the semiconductor laser can be used instead of the light-emitting diode. Furthermore, it is not necessarily needed to pair the light-emitting element and the light-receiving element. For example, the light-emitting element may be an illumination apparatus which illuminates the treatment vessel entirely. Alternatively, the light emitting elements and the light receiving elements can be arranged in a matrix. In that case, the presence or absence of the bubble can be detected two-dimensionally, and the size of the bubble (or the degree of spread of bubble) as well as the bubble shape can be also detected at the same time.

Alternatively, the detection device using an acoustic wave such as ultrasonic waves can be used as the bubble detection device. Similarly to the case of the light-emitting and light-receiving elements, the detection device is set such that the acoustic wave passes through the bubble-formed part. As in the case of light, since the travelling path of the acoustic wave is changed depending on the presence or absence of bubble, the presence or absence of bubble can be detected by detecting the change. Further, the wavelength shift of the acoustic wave due to the Doppler effect can be detected based on the flow rate of the bubble. In this case, the bubble shape can be detected by arranging the acoustic wave devices in a matrix similarly to the light-emitting element and the light-receiving element.

The present embodiment is based on the elemental analysis apparatus of the first embodiment. The present embodiment can be provided as a construction wherein the bubble detection device and the control apparatus are added to the elemental analysis apparatus of the second embodiment. When the analysis apparatus of the second embodiment is used, the state of the bubble is drastically changed by electrode angles at which the first electrodes and the second electrodes are immersed in the liquid. For this reason, controlling the optical detection device depending on the bubble is further needed in the analysis apparatus of the second embodiment. By using the gas detection device and the control apparatus, it is possible to understand the state of the bubble and to introduce the plasma light to the optical detection device accurately.

Since the elemental analysis apparatus according to one embodiment of the present invention enables the elemental analysis to be conducted with low power consumption and high sensitivity, the apparatus can be used for, for example, management of water quality of water and sewerage, wastewater management in a factory, concentration management of cultivation liquid for a farm or cultivation of flower. Further, the elemental analysis apparatus according to another embodiment of the present invention is excellent in portability and makes it possible to analyze, for example, water quality in various places with ease.

What is claimed is:

1. An elemental analysis apparatus for analyzing a liquid, comprising:
    first and second electrodes adapted to at least partially be placed in the liquid, respectively;
    a flow path through which a gas passes for generating a bubble in the liquid;
    an insulator covering the first electrode and the flow path, the insulator having an opening from which the first electrode and the flow path are exposed;
    a gas supply which supplies the gas to the flow path, an amount of the gas to be supplied being so determined to generate the bubble which is able to cover the first electrode exposed through the opening for generation of plasma in the bubble;
    a power supply which supplies voltage between the first electrode and the second electrode to generate the plasma in the bubble, and
    a first optical detector which detects an emission spectrum of the plasma.

2. The elemental analysis apparatus according to claim 1, wherein
    the first electrode has the opening of the flow path, and
    the flow path, connected between the opening and the gas supply, runs inside the first electrode.

3. The elemental analysis apparatus according to claim 1, wherein
    the first electrode has a cylindrical shape having the opening of the flow path,
    the flow path, connected between the opening and the gas supply, runs inside the first electrode, and the insulator is in direct contact with an outer surface of the first electrode.

4. The elemental analysis apparatus according to claim 1, further comprising a treatment vessel to be filled with the liquid, a part of the treatment vessel being optically transparent.

5. The elemental analysis apparatus according to claim 1, wherein the gas supply includes gas sources respectively containing gases to be selectively supplied to the flow path, types of the gases being different from each other.

6. The elemental analysis apparatus according to claim 1, wherein the first optical detector is disposed on a side opposite to a side to which the bubble grows.

7. The elemental analysis apparatus according to claim 1, wherein the insulator is optically transparent.

8. The elemental analysis apparatus according to claim 7, wherein the insulator comprises quartz.

9. The elemental analysis apparatus according to claim 1, further comprising a second optical detector that monitors the bubble, wherein
the first optical detector is activated to detect the emission spectrum of the plasma, in response to a result of monitoring the bubble by the second optical detector.

10. The elemental analysis apparatus according to claim 1, further comprising:
a second optical detector which detects an emission spectrum of the plasma, and
a third optical detector that monitors the bubble, wherein
at least one of the first and second optical detectors is activated to detect the emission spectrum of the plasma, in accordance with a result of monitoring the bubble by the third optical detector.

11. The elemental analysis apparatus according to claim 1, wherein the power supply supplies the voltage between the first electrode and the second electrode when the bubble covers the first electrode exposed through the opening.

12. The elemental analysis apparatus according to claim 1, wherein
the first electrode projects from the opening, and
the amount of the gas to be supplied to the flow path is so determined to generate the bubble which is able to cover the first electrode projecting from the opening.

13. The elemental analysis apparatus according to claim 1, wherein
no portion of the first electrode projects from the opening, and
the amount of the gas to be supplied to the flow path is so determined to generate the bubble which is able to occupy the opening.

* * * * *